(12) United States Patent
Reynolds et al.

(10) Patent No.: US 7,757,691 B2
(45) Date of Patent: Jul. 20, 2010

(54) THERAPEUTIC MEDICAL APPLIANCE DELIVERY AND METHOD OF USE

(75) Inventors: Jason Reynolds, Charlotte, NC (US); Tony D. Alexander, Charlotte, NC (US); Ji Hwan You, Charlotte, NC (US)

(73) Assignee: Merit Medical Systems, Inc., South Jordan, UT (US)

( * ) Notice: Subject to any disclaimer, the term of this patent is extended or adjusted under 35 U.S.C. 154(b) by 623 days.

(21) Appl. No.: 10/567,508

(22) PCT Filed: Aug. 9, 2004

(86) PCT No.: PCT/US2004/025682

§ 371 (c)(1),
(2), (4) Date: Feb. 7, 2006

(87) PCT Pub. No.: WO2005/013808

PCT Pub. Date: Feb. 17, 2005

(65) Prior Publication Data

US 2006/0217759 A1    Sep. 28, 2006

(51) Int. Cl.
*A61M 16/00* (2006.01)
(52) U.S. Cl. ............................ 128/207.15; 623/1.11
(58) Field of Classification Search ............ 606/142, 606/143, 213, 108; 623/1.11, 1.12, 1.16, 623/23.64–23.71; 604/158; 227/19; 128/200.24, 128/207.15
See application file for complete search history.

(56) References Cited

U.S. PATENT DOCUMENTS

| | | | |
|---|---|---|---|
| 3,196,876 A | | 7/1965 | Roberts et al. |
| 4,606,330 A | | 8/1986 | Bonnet |
| 4,795,434 A | * | 1/1989 | Kujawski .................. 604/159 |

(Continued)

FOREIGN PATENT DOCUMENTS

EP    0 516 189 A1    12/1992

(Continued)

OTHER PUBLICATIONS

International Search Report for PCT/US2004/025682 completed Jul. 6, 2005.

(Continued)

*Primary Examiner*—Todd E Manahan
*Assistant Examiner*—Jennifer L Hornberger
(74) *Attorney, Agent, or Firm*—Stoel Rives LLP (57) ABSTRACT

The present invention, in an exemplary embodiment, provides a therapeutic medical appliance, delivery device and method of use. In particular, plug therapeutic medical appliances are provided that allow for the interventional treatment of pulmonary disorders such as defects characterized by pulmonary blebs and/or diffused destructive parenchymal disease. The plug therapeutic medical appliances themselves combine many of the excellent characteristics of both silicone and metal therapeutic medical appliances while eliminating the undesirable ones. In particular, these therapeutic medical appliances are preferably self-expanding in nature and allow the predetermined differential selection of relative hardness/softness of regions of the therapeutic medical appliance to provide additional patient comfort. An exemplary embodiment also provides a family of delivery devices that facilitate flexibility, durability and/or proper installation of one or more medical appliances in a single procedure. Moreover, the preferred embodiment of the delivery device provides for the reloading of the delivery device with additional medical appliances for additional interventional procedures.

46 Claims, 8 Drawing Sheets

U.S. PATENT DOCUMENTS

| | | | |
|---|---|---|---|
| 4,893,623 A | 1/1990 | Rosenbluth | |
| 5,019,085 A | 5/1991 | Hillstead | |
| 5,159,920 A | 11/1992 | Condon et al. | |
| 5,249,585 A | 10/1993 | Turner et al. | |
| 5,320,617 A | 6/1994 | Leach | |
| 5,409,453 A | 4/1995 | Lundquist et al. | |
| 5,503,635 A * | 4/1996 | Sauer et al. | 606/153 |
| 5,514,093 A | 5/1996 | Ellis et al. | |
| 5,549,644 A | 8/1996 | Lundquist et al. | |
| 5,588,949 A | 12/1996 | Taylor et al. | |
| 5,601,591 A | 2/1997 | Edwards et al. | |
| 5,603,698 A | 2/1997 | Roberts et al. | |
| 5,667,522 A | 9/1997 | Flomenblit et al. | |
| 5,735,859 A * | 4/1998 | Fischell et al. | 606/108 |
| 5,746,692 A | 5/1998 | Bacich et al. | |
| 5,782,838 A | 7/1998 | Beyar et al. | |
| 5,817,102 A | 10/1998 | Johnson et al. | |
| 5,824,058 A | 10/1998 | Ravenscroft et al. | |
| 5,833,694 A | 11/1998 | Poncet | |
| 5,902,333 A | 5/1999 | Roberts et al. | |
| 5,984,964 A | 11/1999 | Roberts et al. | |
| 6,019,778 A | 2/2000 | Wilson et al. | |
| 6,086,528 A | 7/2000 | Adair | |
| 6,162,231 A | 12/2000 | Mikus et al. | |
| 6,302,906 B1 | 10/2001 | Goicoechea et al. | |
| 6,322,586 B1 | 11/2001 | Monroe et al. | |
| 6,325,790 B1 | 12/2001 | Trotta | |
| 6,369,355 B1 | 4/2002 | Saunders | |
| 6,375,676 B1 | 4/2002 | Cox | |
| 6,451,025 B1 | 9/2002 | Jervis | |
| 6,517,569 B2 | 2/2003 | Mikus et al. | |
| 6,569,085 B2 | 5/2003 | Kortenbach et al. | |
| 6,599,314 B2 | 7/2003 | Mathis | |
| 6,623,491 B2 | 9/2003 | Thompson | |
| 6,626,902 B1 * | 9/2003 | Kucharczyk et al. | 606/41 |
| 6,656,211 B1 | 12/2003 | DiCaprio | |
| 6,656,214 B1 | 12/2003 | Fogarty et al. | |
| 6,663,660 B2 | 12/2003 | Dusbabek et al. | |
| 6,663,880 B1 | 12/2003 | Roorda et al. | |
| 6,669,716 B1 | 12/2003 | Gilson et al. | |
| 6,669,718 B2 | 12/2003 | Besselink | |
| 6,669,720 B1 | 12/2003 | Pierce | |
| 6,673,101 B1 | 1/2004 | Fitzgerald et al. | |
| 6,676,692 B2 | 1/2004 | Rabkin et al. | |
| 6,676,693 B1 | 1/2004 | Belding et al. | |
| 6,689,157 B2 | 2/2004 | Madrid et al. | |
| 6,695,809 B1 | 2/2004 | Lee | |
| 6,695,812 B2 | 2/2004 | Estrada et al. | |
| 6,695,862 B2 | 2/2004 | Cox et al. | |
| 6,699,274 B2 | 3/2004 | Stinson | |
| 6,699,277 B1 | 3/2004 | Freidberg et al. | |
| 6,702,849 B1 | 3/2004 | Dutta et al. | |
| 6,702,850 B1 | 3/2004 | Byun et al. | |
| 6,723,071 B2 | 4/2004 | Gerdts et al. | |
| 6,723,113 B1 | 4/2004 | Shkolnik | |
| 6,726,712 B1 | 4/2004 | Raeder-Devens et al. | |
| 6,733,521 B2 | 5/2004 | Chobotov et al. | |
| 6,736,828 B1 | 5/2004 | Adams et al. | |
| 6,743,219 B1 | 6/2004 | Dwyer et al. | |
| 6,746,423 B1 | 6/2004 | Wantink | |
| 6,749,627 B2 | 6/2004 | Thompson et al. | |
| 6,752,819 B1 | 6/2004 | Brady et al. | |
| 6,752,825 B2 | 6/2004 | Eskuri | |
| 6,755,855 B2 | 6/2004 | Yurek et al. | |
| 6,761,703 B2 | 7/2004 | Miller et al. | |
| 6,761,708 B1 | 7/2004 | Chiu et al. | |
| 6,761,733 B2 | 7/2004 | Chobotov et al. | |
| 6,773,446 B1 | 8/2004 | Dwyer et al. | |
| 6,773,447 B2 | 8/2004 | Laguna | |
| 6,773,448 B2 | 8/2004 | Kusleika et al. | |
| 6,780,182 B2 | 8/2004 | Bowman et al. | |
| 6,780,199 B2 | 8/2004 | Solar et al. | |
| 6,790,220 B2 | 9/2004 | Morris et al. | |
| 6,790,223 B2 | 9/2004 | Reever | |
| 6,800,081 B2 | 10/2004 | Parodi | |
| 6,802,846 B2 | 10/2004 | Hauschild et al. | |
| 6,802,849 B2 | 10/2004 | Blaeser et al. | |
| 6,808,529 B2 | 10/2004 | Fulkerson | |
| 7,137,993 B2 * | 11/2006 | Acosta et al. | 623/1.11 |
| 2002/0161425 A1 | 10/2002 | Hemerick et al. | |
| 2002/0183763 A1 | 12/2002 | Callot et al. | |
| 2002/0198593 A1 | 12/2002 | Gomez et al. | |
| 2003/0144671 A1 | 7/2003 | Brooks et al. | |

FOREIGN PATENT DOCUMENTS

| | | |
|---|---|---|
| EP | 1 036 550 A2 | 9/2000 |
| JP | 2001-299932 | 10/2001 |
| WO | WO 97/14456 | 4/1997 |
| WO | WO 97/40739 | 11/1997 |
| WO | WO 02/083038 A2 | 10/2002 |

OTHER PUBLICATIONS

Written Opinion of the International Searching Authority form PCT/US2004/025682 mailed Jul. 6, 2005.

* cited by examiner

THERAPEUTIC MEDICAL APPLIANCE DELIVERY AND METHOD OF USE

FIELD OF INVENTION

The present invention relates generally to medical devices directed to interventional treatment, and more particularly to plugs, delivery devices and methods for utilizing these plugs in the treatment of pulmonary disorders such as defects characterized by pulmonary blebs and/or diffused destructive parenchymal disease.

BACKGROUND OF THE INVENTION

Therapeutic medical appliances are devices that are inserted into a vessel or passage to keep the lumen open and prevent closure due to a stricture, external compression, or internal obstruction. In particular, therapeutic medical appliances are commonly used to keep blood vessels open in the coronary arteries and they are frequently inserted into the ureters to maintain drainage from the kidneys, the bile duct for pancreatic cancer or cholangiocarcinoma or the esophagus for strictures or cancer. Vascular as well as not vascular therapeutic medical applianceing has evolved significantly; unfortunately there remain significant limitations with respect to the technology for producing therapeutic medical appliances suitable to various portions of a patient's anatomy.

Unfortunately, because of the topology of the human lungs generally and the various lobes in particular, traditional therapeutic medical applianceing is not effective in the treatment of pulmonary blebs and/or diffused destructive parenchymal disease. In most cases, attempts are made to section off lung tissue, which generally results in fluid retention and concomitant complications. Even if there was a way to delivery a therapeutic medical appliance to one bleb, it would require multiple procedures to address the common presence of multiple blebs.

Physicians have attempted to improve lung function in patients with emphasyma by utilizing lung volume reduction procedures. The principal behind such procedures is that if the increased residual volume created by the bullous of disease could be reduced, the patients' respiratory limitations could be alleviated. Lung volume reduction procedures are very invasive and are only available to a minority of emphysema patients and require significant post surgical care and rehabilitation. Alternative systems have attempted to install valve systems that allow for the alleviation of respiratory limitations by closing blebs without the undesireable back filling of the closed areas. Regrettably, the valve system has a relatively short useful life, and therefore limited applicability, since patients with emphysema also have chronic bronchitis and thus lots of secretions in their airways to obstruct the valves. Moreover, placement of these valves requires invasive procedures as well.

Therefore there remains a need for a therapeutic medical appliance that can be placed in the segmental airways so as to reduce the residual volume and improve ventilation in a less invasive manner. Chiefly, there remains an existing need for a device and delivery method for installing the device in the lungs of a patient to treat pulmonary blebs or other suitable abnormalities. In particular, there is a need for a specialized therapeutic medical appliance designed to plug fissures or other abnormal anatomical openings. Moreover, there is an existing need for an interventional technique that allows for the delivery of multiple therapeutic medical appliances during a single procedure, without having to remove the delivery device. A need also remains for a delivery device that can be reloaded with a plurality of therapeutic medical appliances. There also remains a need for a method of treating pulmonary blebs that prevents disease recurrence in, aggravation and/or deterioration of the patient's pulmonary health.

SUMMARY OF EXEMPLARY EMBODIMENTS

It is a principal purpose of the present invention to provide a specialized medical appliance, in accordance with an exemplary embodiment of the present invention, which can be indicated for a number of disorders, including particularly the treatment of pulmonary disorders such as defects characterized diffused destructive parenchymal disease. In particular, it is an objective of a preferred embodiment in accordance with the present invention to provide a medical appliance that is easily installed, yet in alternative embodiments, removable. Moreover the medical appliance in accordance with this embodiment of the present invention would not cause material infections and may be capable of reducing infection. Therefore, a principal objective of a preferred embodiment in accordance with the present invention is to provide a prosthesis that is suitable for both permanent and temporary use while being easy to insert, reposition and remove.

A principal objective of a preferred embodiment of the present invention is to provide a medical appliance that may be stamped from preferably a single material that is capable of maintaining its axial working length when radially compressed. To this end, the therapeutic medical appliance does not have a seam that could aggravate luminal tissue. In particular, a medical appliance in accordance with the present invention is formed using a tool that molds the medical appliance's outer contour as well as its interstices.

It is yet another objective of an exemplary embodiment of the present invention to provide a medical appliance that can be indicated for the treatment of pulmonary blebs and improve the way clinicians treat malignant obstructions.

Still another objective of the present invention is to provide a medical appliance and method for installing the medical appliance that is economical and suitable for routine purposes. Moreover, a preferred embodiment of the medical appliance has a self-sealing membrane at one or both end to allow for the closing off of the target area while allowing the physician to introduce and/or evacuate material there through.

A principal objective of an exemplary therapeutic medical appliance in accordance with the present invention is to provide a family of medical appliances where the relative hardness/softness of regions of the therapeutic medical appliance can differ from other regions of the therapeutic medical appliance to provide additional patient comfort and resistance to radial forces.

An additional objective in accordance with an exemplary embodiment is to provide a family of medical appliances with novel interstice configurations that facilitate flexibility, durability and/or proper installation.

Yet another principal objective of an exemplary delivery system in accordance with the present invention to provide a device that can facilitate the precise delivery of the medical appliances in a safe and repeatable fashion. In the furtherance of this and other objectives, a preferred deployment apparatus allows the physician to concentrate on correct placement without having to estimate extent of deployment. In particular, in a preferred embodiment, the present device has a physical safety mechanism that limits deployment to the critical deployment point (i.e., ~60%). The critical deployment point may range from 5% to 95% but is preferably about 60%. At this point, if the physician is satisfied with placement, she can engage the safety means to what we refer to as the Proceed Orientation (PO) and fully deploy the medical appliance. It is preferred that when the safety mechanism is engaged to the PO, a tactile, visual and/or possible audible indicator sounds to inform the physician that if she deploys the therapeutic medical appliance any further, she can no longer retract the therapeutic medical appliance beyond this point. Though the present therapeutic medical appliance and delivery system eliminates the need for repositioning, such safety features are still preferable. In a preferred embodiment, the slight audible indication is the sound of a tab or stop snapping to allow free deployment of the therapeutic medical appliance.

Still another objective of an exemplary embodiment in accordance with the present invention is to provide a delivery system that allows for the placement of multiple medical appliances during a single procedure without having to first remove the delivery device. Moreover, the delivery device in alternative embodiments may be reloaded by attaching removable medical appliance containing housings thereto.

An additional objective in accordance with an alternative embodiment of the present invention is to provide a delivery system that has an outer tubular member of sufficient cross sectional thickness to define a plurality of longitudinally extending channels for receiving additional utility tools. In the furtherance of this and other objectives, and by way of example only, one such channel could accommodate an ultra thin scope while an alternative channel receives a guidewire, syringe systems, etc. Principally, these channels are suitable for receiving a number of other tools that a physician may need during deployment of a therapeutic medical appliance or therapeutic treatment of target tissue.

Still another objective in accordance with a preferred embodiment of the present invention is to provide a device having direct visualization capabilities directly incorporated into the device.

In addition to the above objectives, an exemplary deployment system preferably has one or more of the following characteristics: (1) biocompatible; (2) compliant with specialized radially expanding plug medical appliances; (3) capable of distal or proximal medical appliance release; (4) smooth and clean outer surface; (5) length of the device variable according to the insertion procedure to be employed; (6) outer dimension as small as possible (depends on the diameter of crimped medical appliance); (7) dimensions of the device must offer enough space for the crimped medical appliance; (8) sufficient flexibility to adapt to anatomical curvatures without loss of ability to push or pull; (9) low friction between the moving parts; (10) sufficient resistance to kinking; (11) good deployment force, ability to reposition partially deployed medical appliance; and (12) sufficiently economical to manufacture so as to make the deployment apparatus disposable.

Further objectives, features and advantages of the invention will be apparent from the following detailed description taken in conjunction with the accompanying drawings.

DETAILED DESCRIPTION OF AN EMBODIMENT

The present invention, in a preferred embodiment, provides a therapeutic medical appliance, the delivery system, and method of using the appliance and delivery system for the treatment of abnormalities, defined by fissures or other openings in the tissue, that require the closing or sealing off of the abnormalities. In particular, the present medical appliance is designed to treat pulmonary blebs and/or diffused destructive parenchymal disease in a patient. To this end, preferred delivery systems allow the user to install the multiple therapeutic medical appliances in various target sites in the segmental airway during a single procedure. In alternative embodiments, the delivery system may be reloadable with one or more additional therapeutic medical appliances.

A preferred therapeutic medical appliance is preferably formed from a composite material selected from the group consisting essentially of Ni, C, Co, Cu, Cr, H, Fe, Nb, O, Ti, plastic, other polymers in general and bioabsorbable polymers, in particular, and combinations thereof. However, alternative materials such as polymeric material, is acceptable provided that the therapeutic medical appliance has radial self-expansion ability. Making specific reference to the memory metal embodiments, the composite material is generally formed into a compressed tube from which the therapeutic medical appliance is etched and is formed on a suitable shaping device to give the therapeutic medical appliance the desired external geometry. Both the synthetic collar techniques and in vitro valuation techniques show the remarkable ability of therapeutic medical appliances in accordance with the present invention to convert acting force into deformation work absorbed by the angled structure, which prevents excessive scaffolding stress and premature material fatigue and accelerated obsolescence.

Though one skilled in the therapeutic medical appliance engineering art, once apprised of the present application, would be able to manufacture a therapeutic medical appliance consistent with the present invention by other methods, a preferred method of manufacturing such therapeutic medical appliances follows. As stated above a composite material is selected and a blank is formed there from. The blank is preferably loser etched and the etch work is generally verified for accuracy using visual recording microscopy. Dimensional measurements are taken to ensure strut thickness, segment angles, zone placement, etc. Moreover, the therapeutic medical appliance is preferably formed on a shaping tool that has substantially the desired contour of the external therapeutic medical appliance dimensions.

In the event the therapeutic medical appliance is to be shaped to the dimensions of a particular lumen, optical photography and/or optical videography of the target lumen may be conducted prior to therapeutic medical appliance formation. Alternatively, a appliance sizing device like the Lumenaide™ designed by Alveolus Inc may be used. The geometry of corresponding zones and connector regions of the therapeutic medical appliance then can be etched and formed in accordance with the requirements of that target lumen.

It should be pointed out that unlike the use of differing shape memory materials to change regions of a therapeutic medical appliance, therapeutic medical appliances in accordance with the present invention can take on an infinite number of characteristic combinations as zones and segments within a zone can be modified by changing angles, segment lengths and segment thicknesses during the etching and forming stages of therapeutic medical appliance engineering or during post formation processing and polishing steps. Moreover, by modifying the geometry of the connectors between zones, addition functionality may be achieved.

Exemplary therapeutic medical appliances in accordance with the present invention may be manufactured for particular lumen in accordance with the manufacturing procedures and containing the characteristics of the devices disclosed in patent application Ser. No. 10/288,615, which has been incorporated in its entirety by this reference.

The therapeutic medical appliance is preferably formed of memory metal and preferably has unique geometrical interstices that are laser etched therein. However, other conventional ways of forming interstices in unitary therapeutic medical appliances, though not equivalent are contemplated and may be employed and would be within the skill set of one in the art.

It cannot be overemphasized, however, that this does not mean the knowledge that changes in the geometry of interstices affect therapeutic medical appliance functionality is currently known in the art. To the contrary, the present inventors discovered the interrelation between interstice geometry, width, length and relative resistance to torsional stress and radial force. In fact, it can be said that the therapeutic medical appliance has circumferential bands extending perpendicularly with respect to the luminal device's longitudinal axis. These bands are referred to generally as zones. A connector connects these bands to one another; the connector is an additional means for adjusting therapeutic medical appliance functionality. In particular, the connector defines a substantially U shaped member, but could define other geometries such as U, V, W, Z, S and X to name a few.

With specific reference being made to a preferred embodiment of the present invention, a therapeutic medical appliance is provided for introduction into a cavity in the anatomy of a patient, the medical appliance comprising a tube with first and second ends and the tube defining a cavity extending between the first and second ends, the medical appliance further comprising a self-sealing membrane coupled about the first end thereof. Preferred self-sealing membrane materials include but are not limited to polymers such as thin rubber.

In the instance where the target location of the therapeutic medical appliance(s) is the lungs, multiple appliances may be needed in order to treat the patient. Unfortunately, heretofore there was no appliance suitable for such treatment, nor was there a device that allows the installation of multiple appliances during a single moderately invasive procedure. A preferred device comprises a longitudinally extending outer tubular member having distal and proximal ends and an interior and exterior surface, the outer tubular member defines a lumen longitudinally extending substantially the distance from the distal end to the proximal end of the outer tubular member and forming a longitudinal expanse there between, running parallel to the longitudinal expanse are a plurality of grooves, the longitudinal expanse forming a lumen there through; a plurality of tracks complementary and slidably coupled with the grooves such that the tracks and the grooves linearly displaceable with respect to the other, the tracks having proximal and distal ends and a plurality of tabs spaced at a functional distance apart from one another between the proximal and distal ends thereof, the plurality of tracks being independent of one another and the outer tubular member, the tabs facing toward the lumen of the outer tubular member; and a handle, coupled with a portion of the outer tubular member, the handle having first and second ends. The handle cooperates with the tracks in a manner consistent with reliable and deliberate delivery of each therapeutic medical appliance. In alternative embodiments, the delivery device comprises a safety system like the one provided in U.S. patent application Ser. No. 10/404,197, which is incorporated in its entirety by this reference. With respect to the safety mechanism, a preferred mechanism is a physical safety mechanism that limits deployment to the critical deployment point (i.e., ~60%). The critical deployment point may range form 5% to 95% but is preferably about 60% or a proportional stop relative to the stent length. At this point, if the physician is satisfied with placement, she con engage the safety means to what we refer to as the Proceed Orientation (PO) and fully deploy the therapeutic medical appliance. It is preferred that when the safety mechanism is engaged to the PO, a sensation or possible audible indicator sounds to inform the physician that if she deploys the therapeutic medical appliance any further, she con no longer retract the delivery system beyond this point and still reposition the therapeutic medical appliance. Certain embodiments (not shown) provide for re-constrainment beyond this point. In addition to or as an alternative, the tabs on the tracks also serve as a safety function to prevent deployment of more than one appliance at a time while also facilitating reloading. Though the present stent and delivery system eliminates the need for repositioning, such safety features are still preferable. In a preferred embodiment, the slight audible indication is the sound of a tab or stop snapping or being traversed to allow free deployment of the appliance. The therapeutic medical appliance may also have seating barbs for retention.

The distal end of the device may be configured such that a portion of the distal region is removable, preferably including the distal portions of the tracks such that a housing containing additional therapeutic medical appliances can be coupled with the device to form a reloadable delivery device. Alternatively, the device may be reloaded with a single appliance containing distal tip, which can be screwed onto the device or coupled with the device by other conventional means.

Making specific reference to the FIGS, a therapeutic medical appliance and delivery device are provided in various embodiments.

Figure 1:
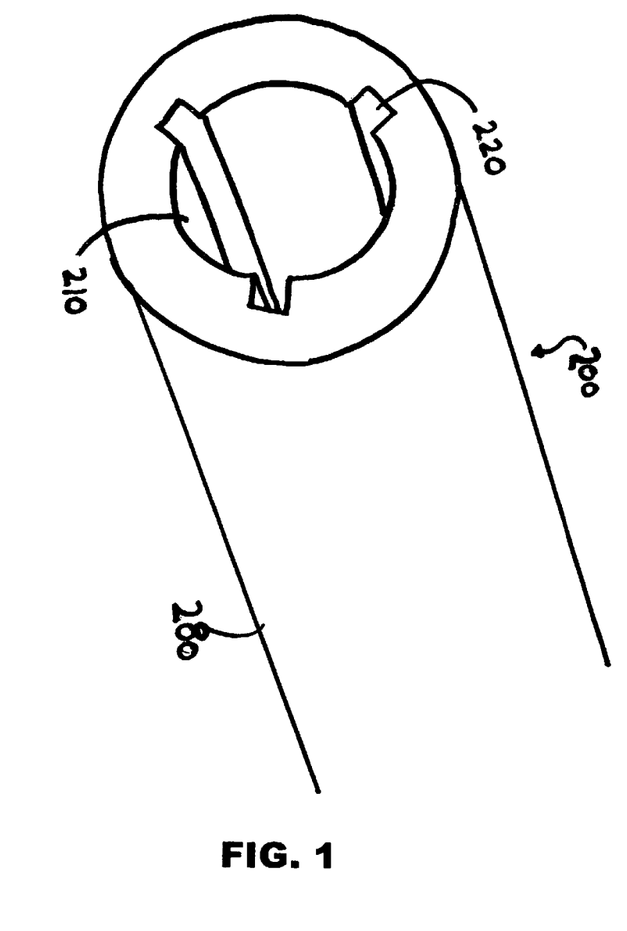
FIG. 1 is a perspective view of the outer tube that constrains the therapeutic medical appliance by radial compression, the tube shown with grooves for receiving the tracks that permit the device to contain a plurality of therapeutic medical appliance while only allowing one stent to be deployed at a time.

Referring generally to the figures where like numerals refer to like parts, varying embodiments of a reusable delivery system, a multifire delivery system and a therapeutic medical appliance are shown. Specifically, referring to FIG. 1, the outer tubular member 200 (alternatively known as an outer sheath) is provided with recesses 220 (alternatively known as grooves) for operatively receiving tracks 300 therein. In the illustrated embodiment, the recesses 220 (grooves) are equi-distantly spaced apart from one another (and complementary and slidably coupled with respective tracks). The outer sheath 200 is certain embodiments can participate in the constrain-ing of the therapeutic medical appliance 100. This is particu-larly relevant in cases where the therapeutic medical appli-ance 100 comprises a memory alloy. The outer sheath 200 has both an interior surface 210 and an exterior surface 280, wherein the groove 220 is formed in the inner surface 210 of the outer sheath 200 and runs longitudinally along a portion thereof.

Figure 2:
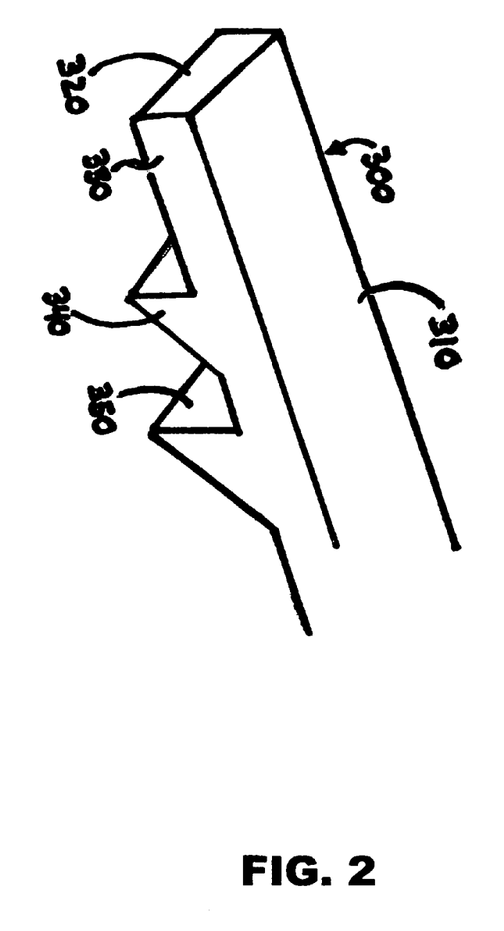
FIG. 2 shows the tracks that ride in the grooves of the outer sheath of FIG. 1, wherein the grooves preferably have unidirectional members that permits the device to deploy a single therapeutic medical appliance and reload multiple times within one procedure.
Figure 3:
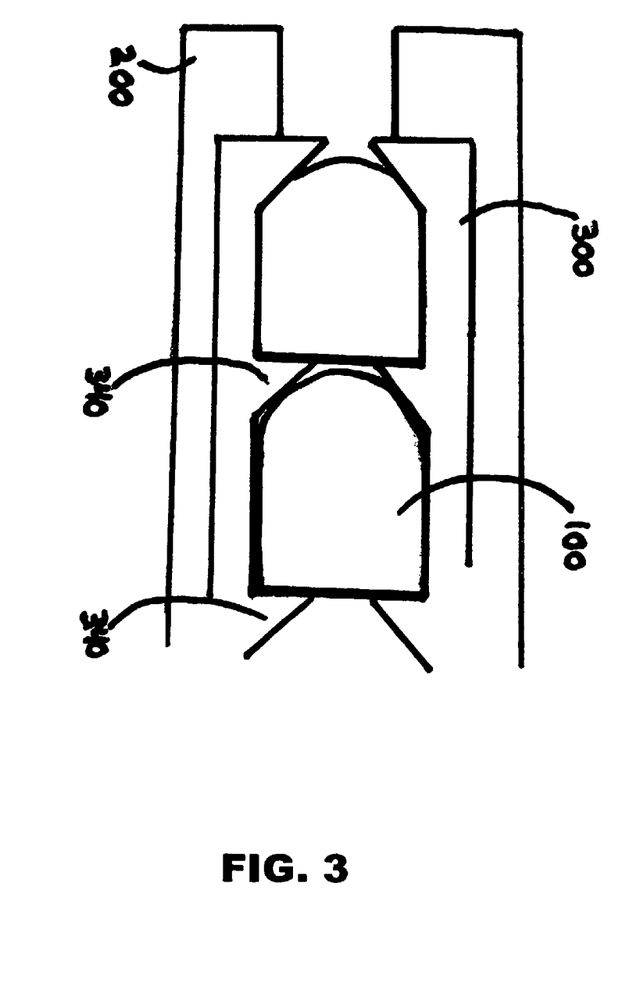
FIG. 3 shows a plurality of therapeutic medical appliances and the relative location of at least two tracks with respect to the therapeutic medical appliances.
Figure 4:
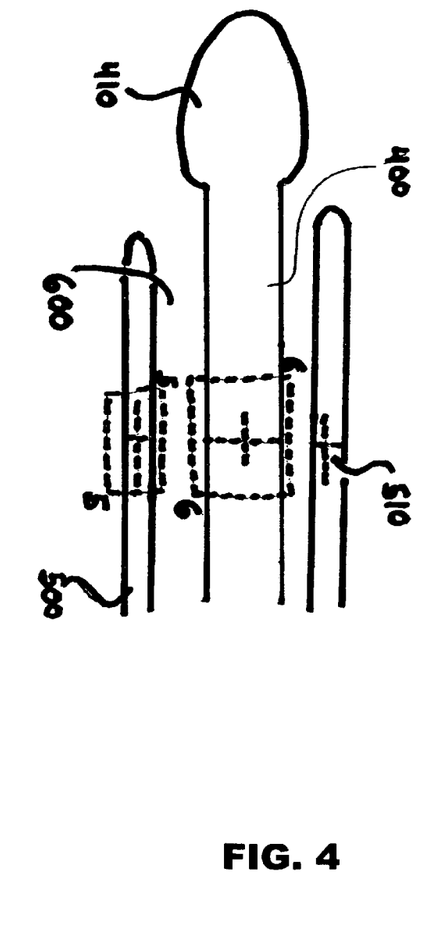
FIG. 4 shows an embodiment of a reloadable delivery device where the therapeutic medical appliance-containing tip snaps onto the outer tube and/or the inner to form the distal region of the delivery device.
Figure 5:
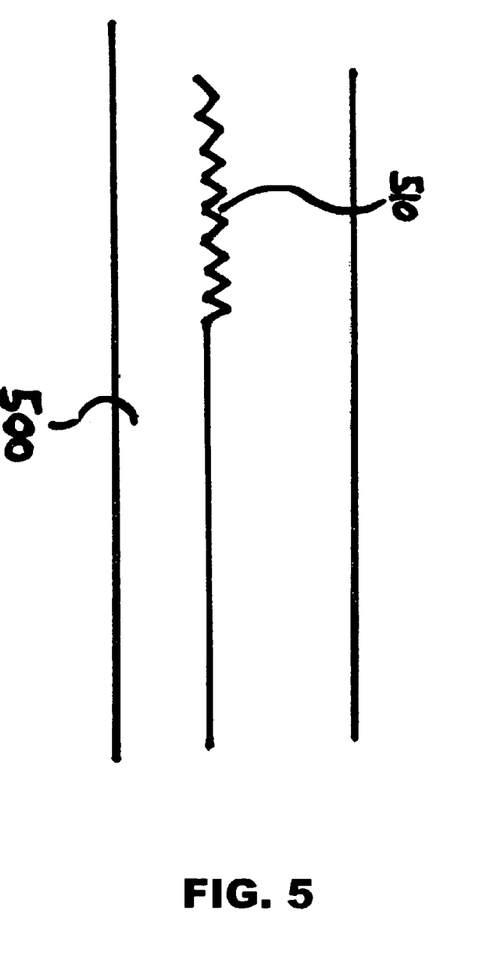
FIG. 5 shows an alternative embodiment of the reloadable delivery device of FIG. 4 where the therapeutic medical appliance-containing tip snaps onto the outer tube and/or the inner to form the distal region of the delivery device.
Figure 6:
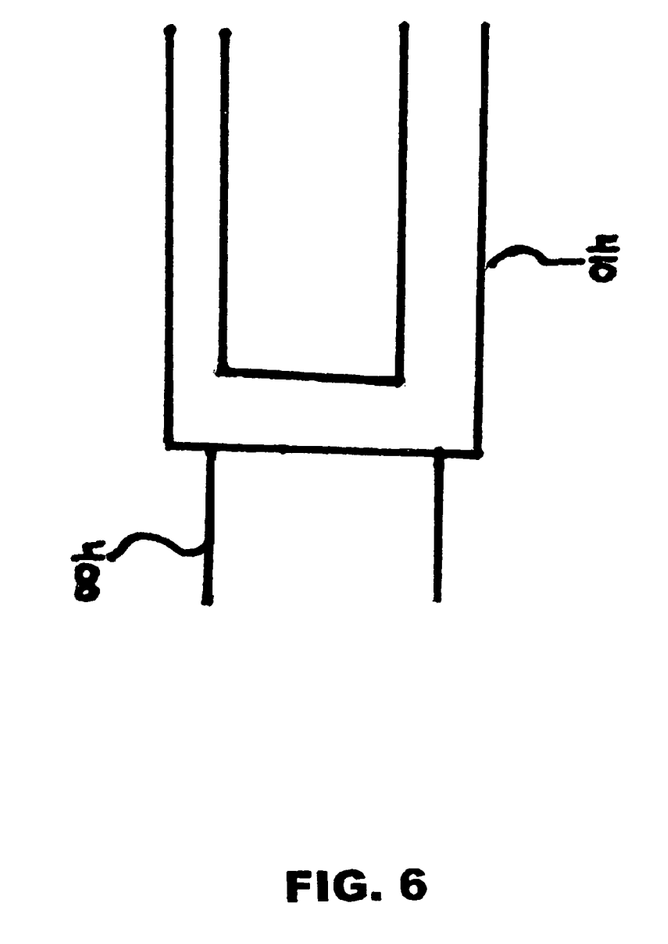
FIG. 6 shows an alternative embodiment of a reloadable delivery device where the therapeutic medical appliance-containing tip has a friction fit coupling with the outer tube and/or the inner to form the distal region of the delivery device.
Figure 7:
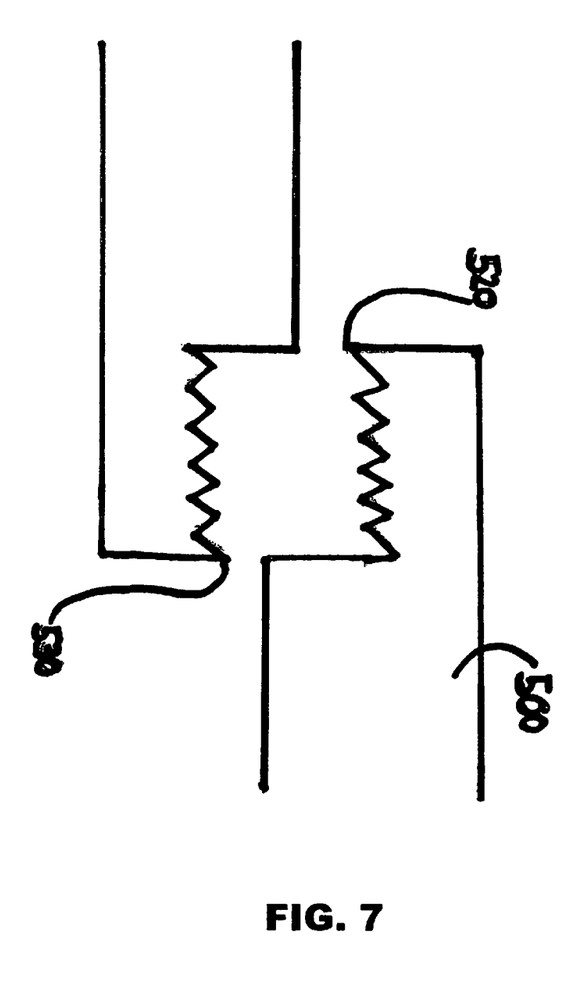
FIG. 7 shows an alternative embodiment of a reloadable delivery device showing the threading components of the reloadable tip.

As shown in FIG. 2, track 300 is operably coupled with groove 220 so as to be slideable therein. The track 300 has a distal end 320, first and second sides 330 and 360. Track 300 also has a top surface 310 that is adjacent groove 220 when in an operable configuration. In the illustrated embodiment, each track and groove has a rectangular cross-section. In certain embodiments, first side 330 and/or second side 360 are in operable communication with groove 220 as well. Moreover, track 300 in preferred embodiments is configured with extensions 340 that preferably have unidirectional faces 350 that are adjacent the proximal region 130 of the thera-peutic medical appliance 100 so as to assist with deployment of the therapeutic medical appliance 100 distally without allowing it to move proximally with respect to other thera-peutic medical appliances. In preferred embodiments, mul-tiple unidirectional surface containing members 340 are pro-vided to allow for the housing of multiple therapeutic medical appliances 100 in the outer sheath 200. The outer sheath 200 may be configured to have one or more grooves 220 so as to receive one or more tracks 300. In the illustrated embodiment, each track 300 is positioned within a respective groove 220 such that the extensions 340 (tabs) extend outwardly from within the groove 220 and into the lumen of the outer sheath 200. As shown in FIG. 3, the therapeutic medical appliance 100 is housed in between the outer sheath 200 directly or indirectly in the event that multiple tracks 300 are provided.

FIGS. 4-7 shows an alternative embodiment of a delivery system in accordance with preferred embodiments of the present invention wherein the system is reusable. In particu-lar, an outer sheath 500 is provided that can be separated at junction 510. Junction 510 may comprise a coupling mecha-nism such as a snap, tension, screw or alternative mating. Shown in more detail in FIGS. 5 & 7 the distal end of the device may be separated from the proximal section. The distal region preferably comprises the section distal the proximal end of the stent, though the distal region may comprise more or less of the outer sheath 500. In embodiments that have an inner sheath 400, the inner sheath may also be removed at a junction similar to that found in the outer sheath 400. In such embodiments the region from the distal tip 410 to a predeter-mined point on the inner sheath 400 may be removed. The coupling of both the inner and the outer sheath can be accom-plished by a variety of coupling means such as those listed above or that may be customary in the fastening art, even though they may not obvious to use in medical devices prior to exposure to this disclosure.

Figure 8:
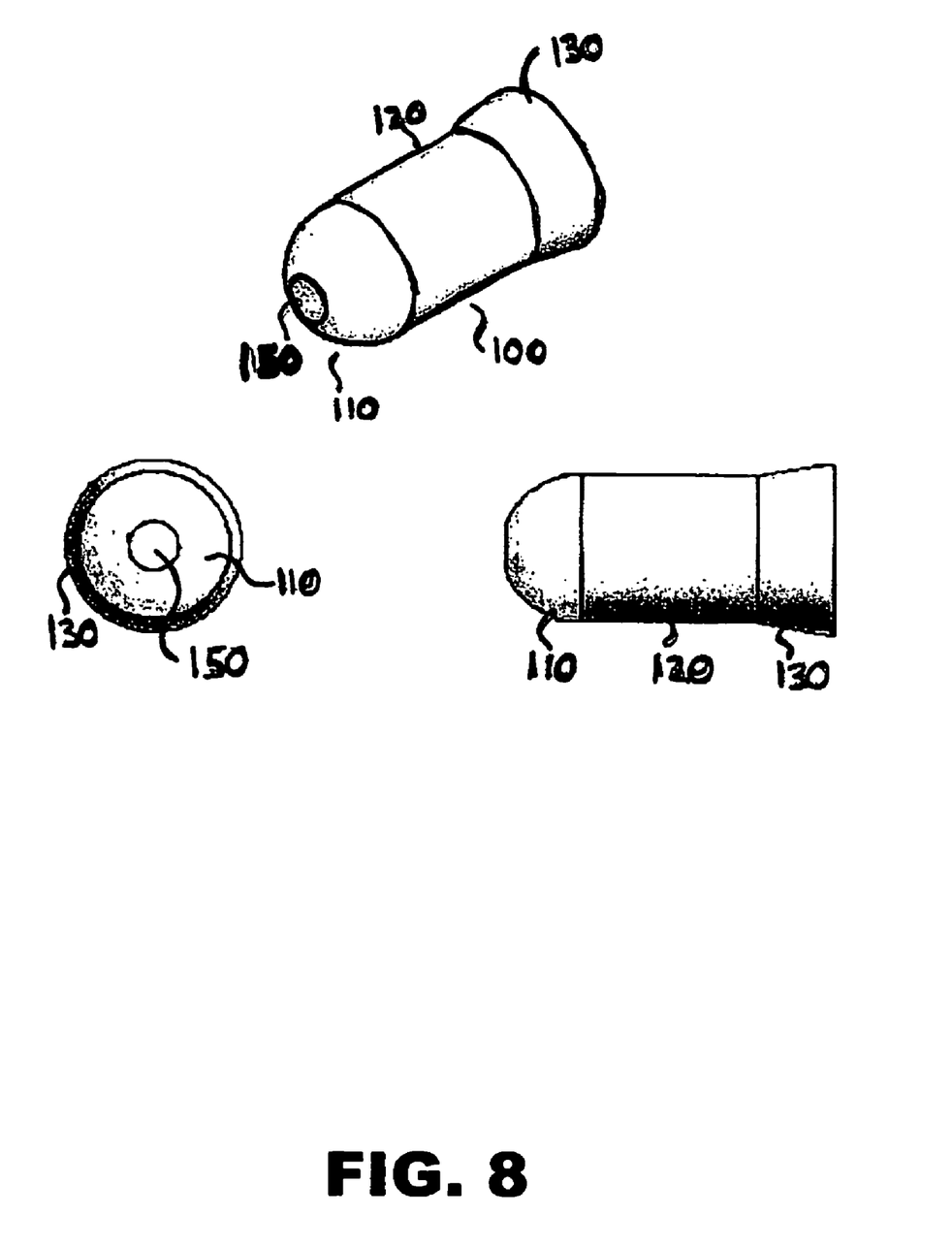
FIG. 8 provides perspective views of the therapeutic medical appliance that does not hove a self-sealing membrane at the distal tip.

Referring now to FIG. 8, a preferred therapeutic medical appliance 100 provides a device having a distal end, 110, a medial region 120 and a proximal end 130. Moreover, in certain embodiments, a self-healing membrane 150 is pro-vided that allows for the penetration thereof without perma-nently damaging the membrane 150. It is also envisioned in certain embodiments that the therapeutic medical appliance may be configured from a bioabsorbable material compatible with mammalian tissue such as a polyglycol.

It should be kept in mind that the handle may be coupled with a portion of the outer sheath or other portions of the delivery system such as the tracks, inner sheath, etc. More-over, in the reusable embodiments, the distal portion may be disposable or reloadable for reuse provided both the distal and the proximal portions of the device are sterilized before sub-sequent use.

In practice the therapeutic medical appliance and delivery device may be used to treat various defects, including but not limited to defects characterized by pulmonary blebs and/or diffused destructive parenchymal disease in a patient, by pro-viding one or more therapeutic medical appliances and plac-ing them about a target site in a lung of a patient generally and the segmental airway in particular. Either independently or through utility channels in the outer tube of the delivery device, an adhesive can be introduced by a syringe into the lung through the self-sealing membrane of the therapeutic medical appliance. An adhesive, which is preferably a local-ized inflammatory response causing and gas-absorbing agent, causes surfaces of lung sections to coalesce and seal the defect. Subsequently, the lung sections are collapsed by evacuating the inflammatory response causing and gas-ab-sorbing agent.

The therapeutic medical appliance may be a simple formed of a any number of materials, including but not limited to a shape memory alloy, polymer, elastimer, etc. The self-sealing membrane is not required.

The present invention may be embodied in other specific forms without departing from its spirit or essential character-istics. The described embodiments are to be considered in all respects only as illustrative, and not restrictive. The scope of the invention is, therefore, indicated by the appended claims, rather than by the foregoing description. All changes, which come within the meaning and range of equivalency of the claims, are to be embraced within their scope.

What is claimed is:

1. A device for allowing a user to deploy a plurality of therapeutic medical appliances in an anatomical lumen of a patient, the device comprising:

a longitudinally extending outer tubular member having distal and proximal ends and an interior and exterior surface, the outer tubular member defines a lumen lon-gitudinally extending substantially the distance from the distal end to the proximal end of the outer tubular mem-ber and forming a longitudinal expanse there between, running parallel to the longitudinal expanse are a plural-ity of grooves, the longitudinal expanse forming a lumen there through, and the outer tubular member having a tip coupled with the distal end;

a plurality of tracks complementary and slidably coupled with the grooves such that the tracks and the grooves are linearly displaceable with respect to the other, each of the tracks having proximal and distal ends and a plurality of tabs spaced axially a functional distance apart from one another along a longitudinal axis between the proxi-mal and distal ends thereof, the tabs facing toward the lumen of the outer tubular member, wherein each tab is configured to engage at least one therapeutic medical appliance; and a handle, coupled with a portion of the outer tubular mem-ber, the handle having first and second ends.

2. The device of claim 1, further including at least one radially self-expanding therapeutic medical appliance carried between tabs of the plurality of tracks, within the lumen of the outer tubular member and thereby maintained in the radially contracted state.

3. The device of claim 2, wherein the outer tubular member when moved longitudinally relative to the track members in a proximal direction away from the selected location, releases the therapeutic medical appliance for radial self-expansion.

4. The device of claim 2, wherein there are at least two therapeutic medical appliances.

5. The device of claim 4, wherein the outer tubular member when moved longitudinally relative to the track members in a proximal direction away from the selected location, releases the distal most therapeutic medical appliance for radial self-expansion and places the distally penultimate therapeutic medical appliance in a ready deployment position within the outer tubular member lumen.

6. The device of claim 2, wherein the handle has a safety means that prevents premature deployment of the at least one therapeutic medical appliance.

7. The device of claim 6, wherein the tabs prevent the uncontrolled proximal migration of the therapeutic medical appliance.

8. The device of claim 1, wherein the outer tubular member defines longitudinally extending channels formed between the exterior and interior surfaces thereof.

9. The device of claim 8, wherein the longitudinally extending channels of the outer tubular member is configured to receive an optical scope.

10. The device of claim 8, wherein the longitudinally extending channels accommodate utility instruments through a lumen thereof.

11. The device of claim 10, wherein the utility instruments are selected from the group consisting of guidewires, optical devices, syringe systems or combinations thereof.

12. The device of claim 11, wherein the syringe system has capabilities selected from the group consisting of thermotherapy, cryotherapy, electrocautery therapy, photodynamic therapy, chemotherapy, adhesive delivery or combinations thereof.

13. The device of claim 12, wherein the syringe system is capable of administering a bioactive product.

14. The device of claim 13, wherein the bioactive product is an adhesive.

15. The device of claim 11, wherein the guidewire has optical capabilities.

16. The device of claim 11, wherein the guidewire has ultrasound capabilities.

17. The device of claim 11, wherein a guidewire is introduced through a portion of the exterior diameter of the outer tubular member.

18. The device of claim 1, wherein the distal tip comprises an interior and an exterior surface and distal and proximal ends.

19. The device of claim 18, wherein the distal tip further comprises a light source.

20. The device of claim 18, wherein the distal tip further comprises utility grooves formed along the exterior surface thereof, which extend substantially between the distal and proximal ends thereof.

21. The device of claim 18, wherein the distal tip defines a plurality of apertures formed there through.

22. The device of claim 1, wherein the outer tubular member is clear.

23. The device of claim 1, wherein the outer tubular member is kink resistant.

24. The device of claim 1, wherein each of the tracks is independent of one another and the outer tubular member.

25. The device of claim 1, wherein each therapeutic medical appliance is configured to be engaged by at least one tab at both a proximal end and a distal end thereof.

26. The device of claim 1, wherein each therapeutic medical appliance is configured to be engaged by a plurality of tabs at both a proximal end and a distal end thereof, independent of one another and the outer tubular member.

27. The device of claim 1, wherein at least three grooves are equidistantly spaced apart from one another and complementary and slidably coupled with respective tracks.

28. The device of claim 1, wherein the plurality of tracks extend longitudinally within the grooves.

29. The device of claim 1, wherein each track includes proximal and distal ends and first and second sides extending therebetween, and wherein each track has a rectangular cross section between both the first and second sides and between the proximal and distal ends.

30. The device of claim 29, wherein each groove has a rectangular cross section and is configured to receive a respective track therein.

31. The device of claim 1, wherein each track is positioned within a respective groove such that the tabs extend outwardly from within the groove and into the lumen of the outer tubular member.

32. A device for allowing a user to deploy a plurality of therapeutic medical appliances in an anatomical lumen of a patient, the device comprising:
a longitudinally extending outer tubular member having distal and proximal ends and an interior and exterior surface, the outer tubular member defines a lumen longitudinally extending substantially the distance from the distal end to the proximal end of the outer tubular member and forming a longitudinal expanse there between, running parallel to the longitudinal expanse are a plurality of grooves, the longitudinal expanse forming a lumen there through;
a plurality of tracks complementary and slidably coupled with the grooves such that the tracks and the grooves are linearly displaceable with respect to the other, each of the tracks having proximal and distal ends and a plurality of tabs spaced axially a functional distance apart from one another along a longitudinal axis between the proximal and distal ends thereof, the tabs facing toward the lumen of the outer tubular member, wherein each tab is configured to engage at least one therapeutic medical appliance; and
a handle, coupled with a portion of the outer tubular member, the handle having first and second ends.

33. The device of claim 32, wherein a therapeutic medical appliance retaining housing is reversibly coupled about the distal end of the device.

34. The device of claim 33, wherein the housing contains one or more therapeutic medical appliances.

35. The device of claim 34, wherein the tabs prevent the uncontrolled proximal migration of the therapeutic medical appliance.

36. The device of claim 32, wherein each of the tracks is independent of one another and the outer tubular member.

37. The device of claim 32, wherein each therapeutic medical appliance is configured to be engaged by at least one tab at both a proximal end and a distal end thereof.

38. The device of claim 32, wherein each therapeutic medical appliance is configured to be engaged by a plurality of tabs at both a proximal end and a distal end thereof.

39. The device of claim 32, wherein at least three grooves are equidistantly spaced apart from one another and complementary and slidably coupled with respective tracks.

40. The device of claim 32, wherein the plurality of tracks extend longitudinally within the grooves.

41. The device of claim 32, wherein each track includes proximal and distal ends and first and second sides extending therebetween, and wherein each track has a rectangular cross section between both the first and second sides and between the proximal and distal ends.

42. The device of claim 41, wherein each groove has a rectangular cross section and is configured to receive a respective track therein.

43. The device of claim 32, wherein each track is positioned within a respective groove such that the tabs extend outwardly from within the groove and into the lumen of the outer tubular member.

44. A device for allowing a user to deploy a plurality of therapeutic medical appliances in an anatomical lumen of a patient, the device comprising:
- a longitudinally extending outer tubular member having distal and proximal ends and an interior and exterior surface, the outer tubular member defines a lumen longitudinally extending substantially the distance from the distal end to the proximal end of the outer tubular member and forming a longitudinal expanse there between, running parallel to the longitudinal expanse are a plurality of grooves, the longitudinal expanse forming a lumen there through; and
- a plurality of tracks independent of one another and the outer tubular member, the plurality of tracks slidably coupled with the grooves such that each of the tracks is independently and axially displaceable within a respective groove, each of the tracks extending longitudinally within a respective groove and having proximal and distal ends and a plurality of tabs spaced axially a functional distance apart from one another between the proximal and distal ends thereof, the tabs facing toward the lumen of the outer tubular member, wherein each tab is configured to engage at least one therapeutic medical appliance.

45. A device for allowing a user to deploy a plurality of therapeutic medical appliances in an anatomical lumen of a patient, the device comprising:
- a longitudinally extending outer tubular member having distal and proximal ends and an interior and exterior surface, the outer tubular member defines a lumen longitudinally extending substantially the distance from the distal end to the proximal end of the outer tubular member and forming a longitudinal expanse there between, running parallel to the longitudinal expanse are a plurality of grooves, the longitudinal expanse forming a lumen there through; and
- a plurality of tracks complementary and slidably coupled with the grooves such that the tracks and the grooves are axially displaceable with respect to the other, each of the tracks having proximal and distal ends and a plurality of tabs spaced axially a functional distance apart from one another along a longitudinal axis between the proximal and distal ends thereof, the tabs facing toward the lumen of the outer tubular member, wherein each therapeutic medical appliance is configured to be engaged by at least one tab at both a proximal end and a distal end thereof, and wherein each track is positioned within a respective groove such that the tabs extend outwardly from within the groove and into the lumen of the outer tubular member.

46. The device of claim 45, wherein each therapeutic medical appliance is configured to be engaged by a plurality of tabs at both a proximal end and a distal end thereof.

* * * * *